United States Patent [19]

Leonard

[11] Patent Number: 4,670,152

[45] Date of Patent: Jun. 2, 1987

[54] PRIMING SYSTEM FOR ULTRAFILTRATION UNIT

[75] Inventor: Ronald J. Leonard, Harvard, Ill.

[73] Assignee: Omnis Surgical Inc., Deerfield, Ill.

[21] Appl. No.: 851,288

[22] Filed: Apr. 10, 1986

Related U.S. Application Data

[63] Continuation of Ser. No. 583,854, Feb. 27, 1984, abandoned.

[51] Int. Cl.$^4$ .............................................. B01D 13/00
[52] U.S. Cl. .................................. 210/651; 210/137; 210/321.4; 210/433.2
[58] Field of Search .................. 422/47, 48; 604/4, 5, 604/6; 210/137, 647, 651, 321.4, 433.2

[56] References Cited

U.S. PATENT DOCUMENTS

| | | | |
|---|---|---|---|
| 3,483,867 | 12/1969 | Markovitz | 128/214 |
| 3,591,493 | 7/1971 | Zeineh | 210/321.2 X |
| 3,783,127 | 1/1974 | Cook et al. | 210/321.1 X |
| 3,788,474 | 1/1974 | Granger et al. | 210/137 |
| 4,209,402 | 6/1980 | Gentles | 210/321.3 X |
| 4,299,705 | 11/1981 | Russell | 210/647 |
| 4,301,118 | 11/1981 | Eddleman et al. | 422/101 |

*Primary Examiner*—Frank Spear
*Attorney, Agent, or Firm*—Paul C. Flattery; Kay H. Pierce; George H. Gerstman

[57] ABSTRACT

A system is disclosed for priming an ultrafiltration unit (10) connected to a blood source, without requiring a pump in the blood line. An ultrafiltration unit (10) is provided having an ultrafiltration membrane which separates a blood compartment from an ultrafiltrate compartment, a blood inlet port (12), a blood outlet port (14), a second inlet port (16) communicating with the ultrafiltrate compartment, and an ultrafiltrate outlet port (18). A feedback tube (38) connects the blood outlet port (14) to the second input port (16). Priming solution (36) is introduced to the blood inlet port (12) and a vacuum is applied to the ultrafiltrate outlet port (18). The priming solution (36) is drawn through the blood compartment, through the ultrafiltrate compartment, out the ultrafiltrate outlet port, and to drain.

11 Claims, 4 Drawing Figures

PRIMING SYSTEM FOR ULTRAFILTRATION UNIT

This application is a continuation of application Ser. No. 583,854, filed 2-27-84, now abandoned.

TECHNICAL FIELD

The present invention concerns a novel system for priming an ultrafiltration unit.

BACKGROUND ART

One of the problems in cardiac bypass surgery is that when the patient's blood has been fully diluted in a bypass circuit with priming solution, addition fluid and cardioplegia solution, the hematocrit has dropped to well under normal values. Since the patient cannot take back his own blood volume and the circuit volume, much of this diluted blood and the patient's blood cells and proteins are left in the oxygenator, heat exchanger and tubing. Recently, a high ultrafiltration hemodialyzer has been used to concentrate this blood by removal of water so that a reasonable volume of the valuable blood constituents can be given back to the patient. In this operational mode, a dialyzer is used only as an ultrafiltrator so that no dialysis solution flow is required. Ultrafiltration is achieved by drawing a vacuum on the dialysate compartment. Sometimes a blood pump is used, but often a tap is made in the circuit downstream of the bypass circuit arterial pump or venous pump in the oxygenator. Thus the circuit and ultrafiltration unit must be primed without a pump.

Dialyzers may require the rinsing of both the blood compartment and the dialysate compartment to prepare the dialyzer and to guard against the possibility of a hypersensitivity reaction in the patient. Of course the rinsing solution must be discarded.

The present invention is particularly applicable to any type of ultrafiltration unit, including a hemoconcentrator, a dialyzer, a diafilter, etc. Such ultrafiltration units generally include an ultrafiltration membrane which separates a blood compartment from an ultrafiltrate compartment. When a dialyzer is used as an ultrafiltration unit, the dialysate compartment of the dialyzer becomes the ultrafiltrate compartment.

It is an object of the present invention to provide a system for priming an ultrafiltration unit without requiring a pump in the blood line.

Another object of the present invention is to provide a system for priming an ultrafiltration unit with a provision for automatically discarding the primng solution without disconnection or reconnection of the blood set.

A further object of the present invention is to provide a system for priming an ultrafiltration unit, enabling the priming and rising of both the blood compartment and the ultrafiltrate compartment, at prescribed flow and volume rates and with an automatic discard of the priming and rinsing solution without disconnection or reconnection of the blood set.

By avoiding the necessity of disconnecting or reconnecting the blood set before, during or after priming and/or rinsing, the sterility compromise concomitant with disconnection or reconnection is obviated.

Other objects and advantages of the present invention will become apparent as the description proceeds.

DISCLOSURE OF THE INVENTION

In accordance with the present invention, a system is provided for priming an ultrafiltration unit, connected to a blood source, without requiring a pump in the blood line. The system includes an ultrafiltration unit having an ultrafiltration membrane which separates a blood compartment from an ultrafiltrate compartment, a blood inlet port, a blood outlet port, a second inlet port communicating with the ultrafiltrate compartment, and an ultrafiltrate outlet port. A feedback tube connects the blood outlet port to the second inlet port, whereby a low pressure can be applied to the ultrafiltrate outlet port and priming solution introduced at the blood inlet port will be drawn through the ultrafiltration unit blood compartment as well as across the membrane and then through the ultrafiltrate compartment and out the ultrafiltrate outlet port.

In the illustrative embodiment, blood inlet tubing is provided for connecting the blood inlet port to a blood source. A first port is provided on the blood inlet tubing for connecting a pressure monitor to the blood inlet tubing. A second port is provided on the blood inlet tubing for connecting a priming solution container to the blood inlet tubing. Blood outlet tubing extends from the blood outlet port. Means are provided for connecting the ultrafiltrate outlet port to a container and means connect the container to a vacuum source.

In the illustrative embodiment, a flow restrictor is interposed in the feedback tube to control the flow rate of the priming solution through the blood path and then into the ultrafiltrate compartment.

In accordance with the present invention, a method is provided for priming an ultrafiltration unit connected to a blood source without requiring a pump in the blood line.

The method comprises the steps of providing an ultrafiltration unit having an ultrafiltration membrane which separates a blood compartment from an ultrafiltrate compartment, a blood inlet port, a blood outlet port, a second inlet port communicating with the ultrafiltrate compartment and an ultrafiltrate outlet port; providing a feedback tube connecting the blood outlet port to the second inlet port; introducing priming solution to the blood inlet port; and applying a low pressure to the ultrafiltrate outlet port to draw the priming solution through the blood compartment as well as across the membrane, through the ultrafiltrate compartment, and out the ultrafiltrate outlet port.

In the illustrative embodiment, the method includes the steps of providing tubing for connecting the blood inlet port to a blood source; connecting a priming solution container to the blood inlet tubing; and prior to introducing the priming solution to the blood inlet port, (1) clamping the tubing upstream of the blood inlet port and introducing priming solution into the tubing upstream of the clamp; and (2) then clamping the tubing downstream of the feedback tube and removing the clamp upstream of the blood inlet port.

A more detailed explanation of the invention is provided in the following description and claims, and is illustrated in the accompanying drawings.

DETAILED DESCRIPTION OF THE ILLUSTRATIVE EMBODIMENT

Figure 1:
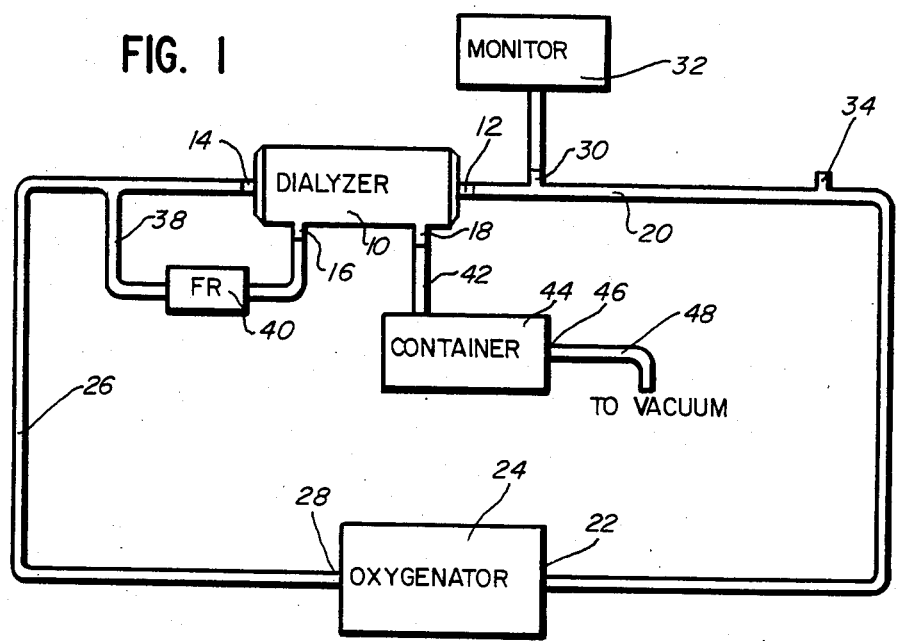
FIG. 1 is a schematic diagram of a system for priming an ultrafiltration unit, constructed in accordance with the principles of the present invention.

Referring to the Figures, an ultrafiltration unit 10, in the exemplary form of a dialyzer, is illustrated having a blood inlet port 12, a blood outlet port 14, a second inlet port 16 and an ultrafiltrate outlet port 18. In a dialyzer, ports 16 and 18 would be the dialysate inlet port and the dialysate outlet port, respectively. Ultrafiltration unit 10 includes a suitable ultrafiltration membrane separating the blood compartment from the ultrafiltrate compartment, as is well-known in the art.

A blood inlet tube 20 connects blood inlet port 12 to the outlet 22 of an oxygenator 24. A blood outlet tube 26 connects the blood outlet port 14 to the inlet 28 of oxygenator 24. This connection could be directly to the oxygenator illustrated or through a cardiotomy reservoir. Additionally, blood might be introduced into a blood bag or other container directly from the hemoconcentrator. The illustrated method is for explanation only and not to restrict the choice of blood inlet source or outlet final destination.

Blood inlet tube 20 includes a first port 30 for enabling the connection of a pressure monitor 32 to the blood inlet tube 20. The blood inlet tube 20 also has a second port 34 for enabling the connection of a priming solution container 36 (FIGS. 2-4) or rinsing solution container to the blood inlet tube 20.

A feedback tube 38 having a flow restrictor 40 is connected from blood outlet port 14 to the second inlet port 16. The second inlet port 16 communicates with the ultrafiltrate compartment of unit 10. The flow restrictor 40 operates to control the flow rate through the ultrafiltration unit 10 as will be explained below.

A priming solution outlet tube 42 connects ultrafiltrate outlet port 18 to a container 44 with the outlet 46 of container 44 being coupled to a vacuum source via tubing 48. Often the hospital has a wall vacuum which is connected to tubing 48.

Figure 2:
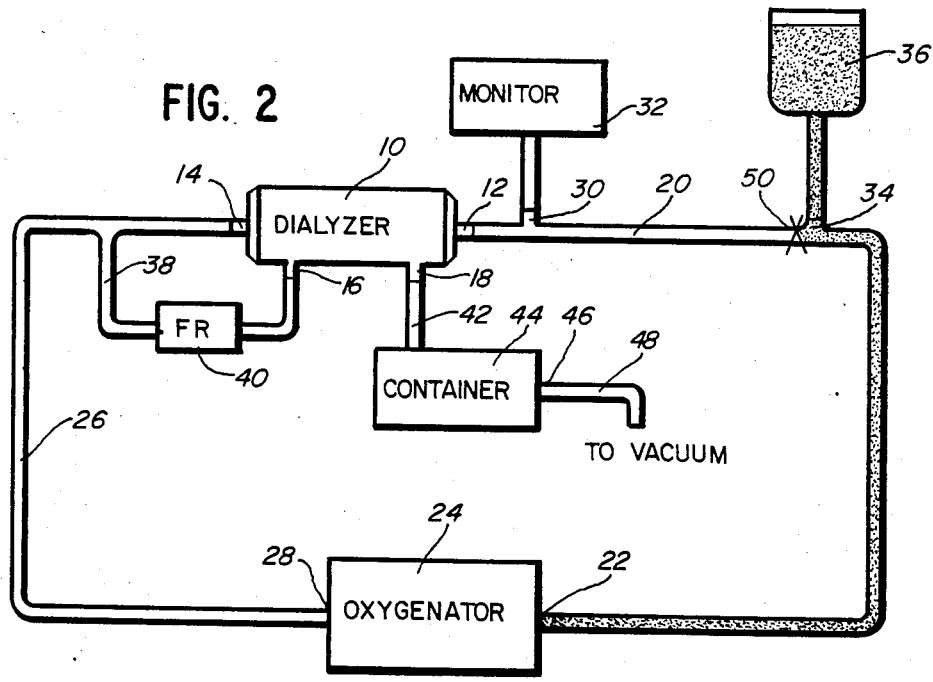
FIG. 2 is a schematic diagram of the system of FIG. 1, after a first step of priming has been accomplished.
Figure 3:
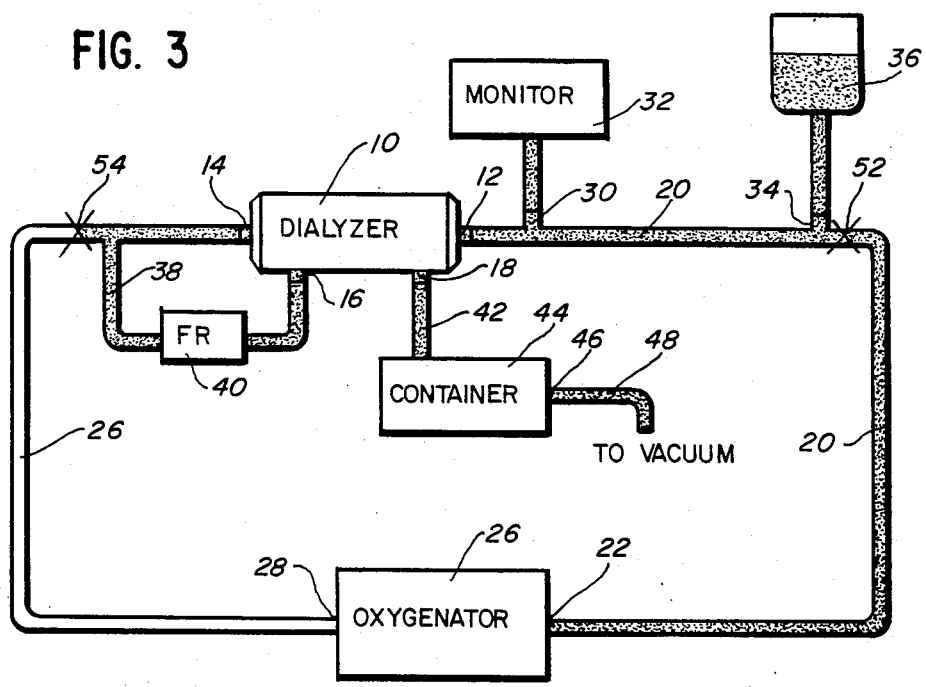
FIG. 3 is a schematic diagram of the system of FIG. 1, after a second step of priming has been accomplished.

The operation of the system will now be explained. Referring to FIG. 2, blood inlet tubing 20 is clamped at point 50 and a container 36 of priming solution such as saline solution, is attached to port 34. The portion of tubing 20 between point 50 and the oxygenator is then primed. Referring to FIG. 3, the clamp is removed at point 50, the blood inlet tubing is clamped at point 52 (upstream of port 34) and the blood outlet tubing 26 is clamped at point 54 (downstream of the feedback tube 38). A vacuum of determined level such as 500 mm mercury is applied at ultrafiltrate outlet port 18. The priming fluid will be drawn from container 36 through the blood compartment of ultrafiltration unit 10, to point 54, through flow restrictor 40, into the ultrafiltrate compartment via second inlet port 16, out of ultrafiltrate outlet port 18 and to drain via tube 48. It can be seen that flow restrictor 40 controls the flow rate of the fluid into the ultrafiltrate compartment.

As the priming fluid flows through the blood compartment of ultrafiltration unit 10, some of it will be ultrafiltered through the membrane. The ultrafiltration unit will be rinsed, flushed and primed with the solution automatically discarded to drain. After about five minutes, in the illustrative embodiment, approximately 800 to 900 ml of priming solution will have passed through the ultrafiltration unit 10.

Figure 4:
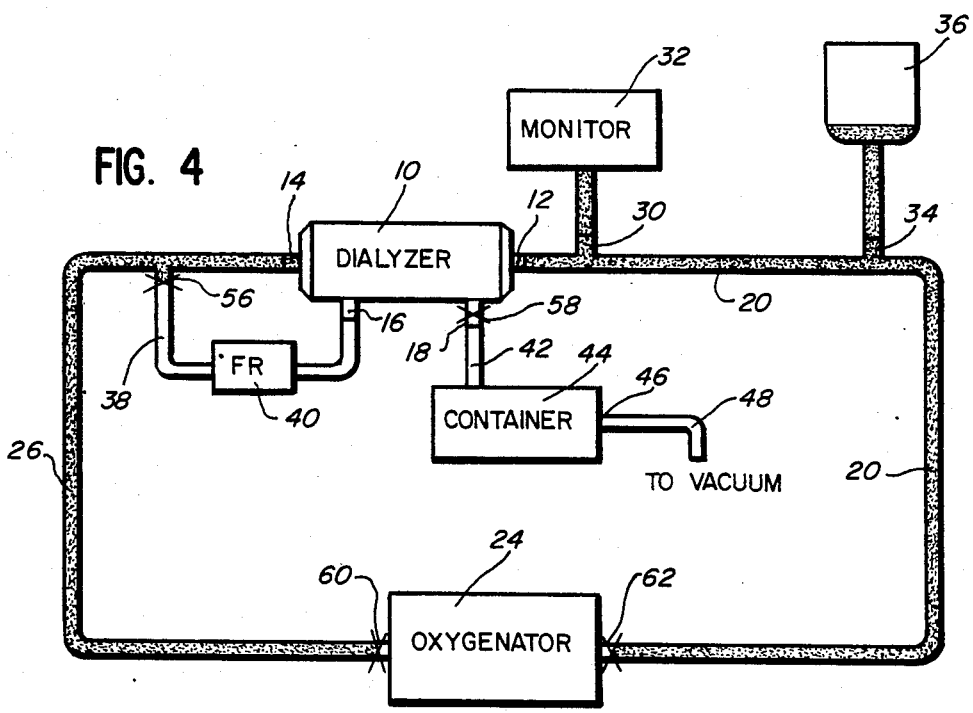
FIG. 4 is a schematic diagram of the system of FIG. 1, after the system has been fully primed.

Referring to FIG. 4, after the ultrafiltration unit 10 has been primed, the clamps at points 52 and 54 are removed and clamps are provided at points 56 and 58, to stop the feedback line and to remove the vacuum. In this manner, the remaining portion of the blood outlet tubing 26 is primed using the remaining solution in container 36 and the line is clamped at points 60 and 62. The system is now ready for use. Clamp 56 remains in place but clamps 58, 60 and 62 are removed and the correct negative pressure is applied at ultrafiltrate outlet port 18 to control ultrafiltration.

It can be seen that a novel system has been disclosed for priming and rinsing an ultrafiltration unit, such as a dialyzer, hemoconcentrator or diafilter, without requiring the use of a pump in the blood line. Both the blood compartment and ultrafiltrate compartment are rinsed at a controlled rate and the solution is automatically discarded without disconnection or reconnection of the blood tubing which could result in sterility compromise.

Although an illustrative embodiment of the invention has been shown as described, it is to be understood that various modifications and substitutions may be made by those skilled in the art without departing from the novel spirit and scope of the present invention.

What is claimed is:

1. In a system for providing and removing priming solution to and from an ultrafiltration unit, connected to a blood source, an ultrafiltration unit having an ultrafiltration membrane which separates a blood compartment from an ultrafiltrate compartment, a blood inlet port, a blood outlet port, and an ultrafiltrate outlet port, the improvement comprising:

a second inlet port communicating with the ultrafiltrate compartment;

a feedback tube connecting the blood outlet port to the second inlet port;

a flow restrictor interposed in the feedback tube to control the flow rate into the ultrafiltrate compartment;

blood inlet tubing for connecting the blood inlet port to a blood source;

a port on the blood inlet tubing for connecting a priming solution container to the blood inlet tubing;

blood outlet tubing extending from the blood outlet port; and flow means for causing the priming solution to flow from the blood compartment through the blood outlet port through the feedback tube into the second inlet port communicating with the ultrafiltrate compartment and out of the ultrafiltrate compartment through the ultrafiltrate outlet port, the flow means including a means for connecting the ultrafiltrate outlet port to a vacuum source.

2. In a system as described in claim 1, in which said ultrafiltration unit is a hemoconcentrator.

3. An ultrafiltration set which can be primed without requiring a pump on the blood line, comprising:

an ultrafiltration unit having an ultrafiltration membrane which separates a blood compartment from an ultrafiltrate compartment;

a blood inlet port;

a blood outlet port;

a second inlet port communicating with the ultrafiltrate compartment;

an ultrafiltrate outlet port;

blood inlet tubing for connecting the blood inlet port to a blood source;

a port on the blood inlet tubing for connecting a priming solution container to the blood inlet tubing;

blood outlet tubing extending from the blood outlet port;

a feedback tube connecting the blood outlet port to the second inlet port;

flow means for causing priming solution introduced at the blood inlet port to be drawn through said blood compartment to said feedback tube and from said feedback tube through said ultrafiltrate compartment and out of the ultrafiltrate outlet port, the flow means including a means for applying a low pressure to the ultrafiltrate outlet port.

4. An ultrafiltration set as described in claim 3, including a flow restrictor interposed in the feedback tube to control the flow rate into the ultrafiltrate compartment.

5. A method for providing and removing priming solution to and from an ultrafiltration unit connected to a blood source comprising the steps of:

providing an ultrafiltration unit having an ultrafiltration membrane which separates a blood compartment from an ultrafiltrate compartment, a blood inlet port, a blood outlet port, a second inlet port communicating with the ultrafiltrate compartment, and an ultrafiltrate outlet port;

providing a feedback tube connecting the blood outlet port to the second inlet port;

introducing priming solution to the blood inlet port; and applying a vacuum to the ultrafiltrate outlet port to draw the priming solution through the blood compartment, through the ultrafiltrate compartment and out the ultrafiltrate outlet port.

6. A method as described in claim 5, including the steps of:

providing tubing for connecting the blood inlet port to a blood source;

connecting a priming solution container to the blood inlet tubing;

prior to introducing priming solution to the blood inlet port, (1) clamping the tubing upstream of the blood inlet port and introducing priming solution into the tubing upstream of the clamp, (2) then clamping the tubing downstream of the feedback tube and removing the clamp upstream of the blood inlet port, whereby the priming solution will be drawn through the blood compartment, through the ultrafiltrate compartment, and out the ultrafiltrate outlet port.

7. In a system for providing and removing priming solution to and from an ultrafiltration unit having an ultrafiltration membrane which separates a first compartment from a second compartment, the first compartment having an inlet port and an outlet port, and the second compartment having an outlet port, the improvement comprising:

an inlet port communicating with the second compartment;

a feedback tube connecting the outlet port of the first compartment to the inlet port of the second compartment;

flow means for causing the primary solution to flow from the first compartment through the outlet port of the first compartment through the feedback tube into the inlet port of the second compartment and out of the second compartment through the outlet port of the second compartment.

8. In a system as described in claim 7, including blood inlet tubing for conecting the inlet port of the first compartment to a blood source, a first port on the blood inlet tubing for connecting a pressure monitor to the blood inlet tubing, a second port on the blood inlet tubing for connecting a priming solution container to the blood inlet tubing, and blood outlet tubing extending from the outlet port of the first compartment.

9. In a system as described in claim 7, wherein said flow means includes means for connecting the outlet port of the second compartment to a container and means for connecfing the container to a vacuum source.

10. In a system as described in claim 7, including a flow restrictor in the feedback tube to control the flow rate into the second compartment.

11. In a system according to claim 7 wherein said flow means includes:

means for applying vacuum pressure to the outlet port of the second compartment, and means for supplying priming solution to the inlet port of the first compartment.

* * * * *